(12) United States Patent
Sun

(10) Patent No.: US 10,441,599 B2
(45) Date of Patent: Oct. 15, 2019

(54) PHARMACEUTICAL COMPOSITION CONTAINING GINKGOLIDE B AND BLOOD PLATELET PROSTAGLANDIN CYCLOOXYGENASE INHIBITOR AND METHOD FOR PREPARATION THEREOF AND USE THEREOF

(71) Applicant: CHENGDU BAIYU PHARMACEUTICAL CO., LTD, Chengdu, Sichuan (CN)

(72) Inventor: Yi Sun, Chengdu (CN)

(73) Assignee: CHENGDU BAIYU PHARMACEUTICAL CO., LTD, Chengdu (CN)

( * ) Notice: Subject to any disclaimer, the term of this patent is extended or adjusted under 35 U.S.C. 154(b) by 0 days.

(21) Appl. No.: 15/513,941

(22) PCT Filed: Sep. 25, 2015

(86) PCT No.: PCT/CN2015/090726
§ 371 (c)(1),
(2) Date: Mar. 23, 2017

(87) PCT Pub. No.: WO2016/045616
PCT Pub. Date: Mar. 31, 2016

(65) Prior Publication Data
US 2017/0273993 A1    Sep. 28, 2017

(30) Foreign Application Priority Data

Sep. 26, 2014 (CN) .......................... 2014 1 0505315

(51) Int. Cl.
*A61K 31/616* (2006.01)
*A61K 31/365* (2006.01)
*A61K 36/16* (2006.01)
*A61P 7/02* (2006.01)

(52) U.S. Cl.
CPC .......... *A61K 31/616* (2013.01); *A61K 31/365* (2013.01)

(58) Field of Classification Search
CPC .... A61K 31/616; A61K 36/16; A61K 31/365; C07D 407/14
USPC .......................................... 424/752; 549/297
See application file for complete search history.

(56) References Cited

FOREIGN PATENT DOCUMENTS

DE          19653100        * 7/1998 ............. A23L 33/16

OTHER PUBLICATIONS

Gardner et al. Blood Coagulation and Fibrinolysis 2007, 18, 787-793.*
EGb 761: ginkgo biloba extract, Ginkor Drugs in R & D 2003, 4(3), 188-193, Abstract.*
Dec. 31, 2015 Search Report issued in International Patent Application No. PCT/CN2015/090726.
Liang, Jing, "The Therapeutic Efficacy of Low-Dose of ASA in Combination with EGb in Blood Rheology Abnormal in Elderly Diseases", Acta Academiae Medicinae Jiangxi, Dec. 31, 2005, vol. 45, No. 3, pp. 105-106 and 109.
Wang, Ruwei et al., "Comparison of anti-platelet aggregation and PAF decrease effect among EGB, Aspirin, and Plavix", Chinese Journal of Clinical Pharmacology and Therapeutics, Sep. 30, 2011, vol. 16, No. 9, pp. 998-1001.
Moon, Sung-Hwan et al., "The Combined Effects of Ginkgo Biloba Extracts and Aspirin on Viability of SK-N-MC, Neuroblastoma Cell Line in Hypoxia and Reperfusion Condition", J Korean Neurosurg Soc., Jan. 2011, vol. 49, No. 1, pp. 13-19.
Wei et al., "Inhibiting Effect of Ginkolide B Derivative (XQ) on Platelet Aggregation Induced by PAF and ADP" Pharmacology College of Nanjing University of Traditional Medicine, pp. 179-181.
Liu et al., "Investigating the Effectiveness of Gingko Leaf Tablet for Treating Aspirion Resistance" Zhejiang Chinese Medicine Journal, May 2010, vol. 45, Issue 5, pp. 320-322.
Jul. 21, 2017 Office Action issued in Chinese Application No. 201510622111.0.
Mar. 29, 2018 Office Action issued in Chinese Application No. 201510622111.0.
Liu et al., "Ginkgo Biloba Leaf Treatment for Asprin Resistance in Clinical Controlled Studies" Zhejiang Chinese Medicine Journal, May 2010, vol. 45, Issue 5, pp. 320-322.
Dec. 5, 2018 Office Action issued in Chinese Application No. 201510622111.0.

* cited by examiner

*Primary Examiner* — Irina Neagu
(74) *Attorney, Agent, or Firm* — Oliff PLC

(57) ABSTRACT

Provided is a pharmaceutical composition containing ginkgolide B and the blood platelet prostaglandin cyclooxygenase inhibitor aspirin, a method for preparation of the pharmaceutical composition and a use thereof. When used together, ginkgolide B and aspirin have a synergistic effect in resisting platelet aggregation.

3 Claims, No Drawings

PHARMACEUTICAL COMPOSITION CONTAINING GINKGOLIDE B AND BLOOD PLATELET PROSTAGLANDIN CYCLOOXYGENASE INHIBITOR AND METHOD FOR PREPARATION THEREOF AND USE THEREOF

TECHNICAL FIELD

The invention relates to a pharmaceutical composition containing Ginkgolide B and method for preparation and use thereof.

BACKGROUND OF THE INVENTION

Aspirin, also known as acetylsalicylic acid, born on Mar. 6, 1899, is an antipyretic and analgesic medication with a long history. It is used to treat cold, fever, headache, toothache, arthralgia and rheumatism. Aspirin can also inhibit platelet aggregation, for preventing and treating ischemic heart disease, angina pectoris, cardiopulmonary infarction and cerebral thrombosis, it is also effective when used in blood vessel forming and bypass transplantation. It is the first anti-aggregation medication to be used for antithrombosis and has been established to treat acute myocardial infarction (AMI), unstable angina pectoris and for prevention of second-stage of myocardial infarction (MI). The principle of the anti-aggregation effect of aspirin is that aspirin inhibits the prostaglandin cyclooxygenase of platelets and prevents the synthesis of thromboxane A2 (TXA2) (TXA2 promotes aggregation of platelets). This effect is irreversible. Specifically, Aspirin irreversibly acetylates the hydroxyl of the 529 serine on the active peptide chain COX-1 of cyclooxygenase (COX) and inactivates COX. This inactivation blocks the conversion of arachidonic acid (AA) to thromboxane A2 (TXA2) and inhibits platelets (PLT) aggregation.

However, among patients who take Aspirin to prevent myocardial infarction and stroke, some people show a low aspirin response and a high incidence risk. The researchers consider that the main reason of the low response is that these patients have developed drug resistance against anticoagulation effect of aspirin. Among the cardiovascular disease patients taking Aspirin, patients with Aspirin resistance are three times more likely to develop myocardial infarction, stroke and even death compared to the others.

Therefore, the poor effect of using aspirin to inhibit platelet aggregation needs to be improved.

SUMMARY OF THE INVENTION

The invention aims to provide a novel pharmaceutical composition with a synergistic effect for overcoming drug resistance of platelet prostaglandin cyclooxygenase inhibitor, such as Aspirin when used for anti-platelet aggregation.

The present invention provides a pharmaceutical composition comprising Ginkgolide B, which contains Ginkgolide B and platelet prostaglandin cyclooxygenase inhibitor, wherein, the platelet prostaglandin cyclooxygenase inhibitor is Aspirin;

wherein, Ginkgolide B in an amount of 1-20 parts by weight and Aspirin in an amount of 50-500 parts by weight.

Preferably, Ginkgolide B in an amount of 5-15 parts by weight and Aspirin in an amount of 100-400 parts by weight. More preferably, Ginkgolide B in an amount of 8-12 parts by weight and Aspirin in an amount of 150-300 by weight. Even more preferably: Ginkgolide B in an amount of 10 parts by weight and Aspirin in an amount of 200 parts by weight.

The present invention also provides a method for preparing the pharmaceutical composition, comprising the following steps:

S1: weighing out raw materials of Ginkgolide B and platelet prostaglandin cyclooxygenase inhibitor Aspirin according to the predetermined parts by weight;

S2: mixing the raw materials, and adding a pharmaceutically acceptable auxiliary to prepare a common pharmaceutical preparation.

Wherein, the platelet prostaglandin cyclooxygenase inhibitor is Aspirin.

Wherein, the pharmaceutical acceptable auxiliary is selected from the group consisting of: starch, pregelatinized starch, lactose, sucrose, talcum powder, dextrin, cyclodextrin, microcrystalline cellulose, croscarmellose sodium, sodium carboxymethyl starch, low substituted hydroxypropyl cellulose, cross-linked povidone, glucose, meglumine, magnesium stearate, dextran, glycerol, ethanol, propylene glycol, polyethylene glycol, mannitol, sorbitol, xylitol, fiber vegetable oil, sodium benzoate, sodium salicylate, hydrochloric acid, citric acid, sodium citrate, sodium dihydrogen phosphate, disodium hydrogen phosphate, gelatin, lecithin and vitamin C.

Wherein, the pharmaceutical formulation comprises: tablet, capsule, soft capsule, oral liquid, granules, pills, dripping pills, powder, paste, pellets, injections, suppository, patch, drop, spray, cream, suspension, tincture, emulsion, solution injection, powder injection, targeting formulation, sustained-release formulation and controlled-release formulation.

The present invention provides use of a pharmaceutical combination of Ginkgolide B and platelet prostaglandin cyclooxygenase inhibitor Aspirin in the manufacturing of a medicament for anti-platelet aggregation.

Wherein the platelet prostaglandin cyclooxygenase inhibitor is Aspirin.

Wherein Ginkgolide B in an amount of 1-20 parts by weight and Aspirin in an amount of 50-500 parts by weight.

Preferably, Ginkgolide B in an amount of 5-15 parts by weight and Aspirin in an amount of 100-400 parts by weight. More preferably, Ginkgolide B in an amount of 8-12 parts by weight and Aspirin in an amount of 150-300 by weight. Even more preferably: Ginkgolide B in an amount of 10 parts by weight and Aspirin in an amount of 200 parts by weight.

The pharmaceutical composition of the present invention comprising Ginkgolide B and Aspirin as active ingredients, which function through different mechanisms for anti-platelet aggregation. Ginkgolide B can remarkably promote the anti-platelet aggregation function of Aspirin, also eliminate/reduce the drug resistance caused by using Aspirin alone. Ginkgolide B and Aspirin work synergistically and provide a better choice for clinical study.

The pharmaceutical composition of the present invention is characterized in a novel formula, simple components, a clear action mechanism, a remarkable effect, and hard to produce tolerance, and a large-scale industrial production can be realized.

The combination use of Ginkgolide B and Aspirin of the present invention results in a synergistic effect and an excellent anti-platelet aggregation effect.

Apparently, according to the above-mentioned disclosure of the present invention, other various modifications, substitutions or alterations can be made without departing from the basic technical concept of the present invention on the basis of the ordinary technical knowledge and common means of the art.

The above disclosure of the present invention is further described in detail in the following embodiments. The following embodiments are for better understanding of the present invention, not to limit the invention to the preferred embodiment. Any technique derived from the present invention, falls within the protection scope of the present invention.

DETAILED DESCRIPTION OF EMBODIMENTS

The Ginkgolide B monomer of the present invention can be obtained by purchasing a commercially available product, or obtained by separating and purifying the Ginkgolide using an existing method; the Aspirin compound can also be obtained by purchasing a commercially available product, or synthesized using an existing method. All monomeric compounds are consistent with the structure of corresponding reference substance, and the purity of all the monomer compounds is over 95% analyzed by HPLC.

Embodiment 1

10 parts by weight of Ginkgolide B
200 parts by weight of Aspirin
Pharmaceutically acceptable auxiliary
Mixing the materials, then adding pharmaceutically acceptable auxiliary to prepare pills according to a conventional process.

Embodiment 2

5 parts by weight of Ginkgolide B
400 parts by weight of Aspirin
Pharmaceutically acceptable auxiliary
Mixing the materials, then adding pharmaceutically acceptable auxiliary to prepare capsule or soft capsule according to a conventional process.

Embodiment 3

20 parts by weight of Ginkgolide B
50 parts by weight of Aspirin
Pharmaceutically acceptable auxiliary
Mixing the materials, then adding pharmaceutically acceptable auxiliary to prepare tablet according to a conventional process.

Embodiment 4

15 parts by weight of Ginkgolide B
100 parts by weight of Aspirin
Pharmaceutically acceptable auxiliary
Mixing the materials, then adding pharmaceutically acceptable auxiliary to prepare oral liquid according to a conventional process.

Embodiment 5

10 parts by weight of Ginkgolide B
300 parts by weight of Aspirin
Pharmaceutically acceptable auxiliary
Mixing the materials, then adding pharmaceutically acceptable auxiliary to prepare dripping pills according to a conventional process.

Embodiment 6

12 parts by weight of Ginkgolide B
150 parts by weight of Aspirin
Pharmaceutically acceptable auxiliary
Mixing the materials, then adding pharmaceutically acceptable auxiliary to prepare spray according to a conventional process.

Embodiment 7

1 parts by weight of Ginkgolide B
500 parts by weight of Aspirin
Pharmaceutically acceptable auxiliary
Mixing the materials, then adding pharmaceutically acceptable auxiliary to prepare solution injection or powder injection according to a conventional process.

Embodiment 8

10 parts by weight of Ginkgolide B
200 parts by weight of Aspirin
Pharmaceutically acceptable auxiliary
Mixing the materials, then adding pharmaceutically acceptable auxiliary to prepare sustained-release formulation and controlled-release formulation according to a conventional process.

Embodiment 9

10 parts by weight of Ginkgolide B
200 parts by weight of Aspirin
Pharmaceutically acceptable auxiliary
Mixing the materials, then adding pharmaceutically acceptable auxiliary to prepare targeting formulation according to a conventional process.

Embodiment 10

10 parts by weight of Ginkgolide B
200 parts by weight of Aspirin
Pharmaceutically acceptable auxiliary
Mixing the materials, then adding pharmaceutically acceptable auxiliary to prepare granules or suspension according to a conventional process.

The beneficial effects of the present invention are further described by following experimental examples.

EXPERIMENTAL EXAMPLE 1

Study of Composition of Ginkgolide B and Platelet Prostaglandin Cyclooxygenase Inhibitor in Inhibition of Rabbit Platelet Aggregation Effect 1 Materials and Methods 1.1. Experimental Animals:

128 Japanese large-ear white rabbits with a weight of $(2.0\pm0.2)$ kg, half male and half female, were provided by Chongqing Medical University Experimental Animal Center [animal certification number: XCXK (Yu) 20020001].

1.2. Experimental Medicine:

The following proportions are in weight ratio.

Ginkgolide B (CHENGDU BAIYU TECHNOLOGY PHARMACY CO., LTD), Aspirin (Bayer, lot number: 120504), Jinnaduo injection (Ginkgolide extraction injection), Composition 1 (Jinnaduo:Aspirin=10:200), Composition 2 (Ginkgolide B:Aspirin=10:200), Composition 3 (Ginkgolide B:Aspirin=1:50), Composition 4 (Ginkgolide B:Aspirin=20:50), Composition 5 (Ginkgolide B:Aspirin=1:500), Composition 6 (Ginkgolide B:Aspirin=15:400), Composition 7 (Ginkgolide B:Aspirin=15:100), Composition 8 (Ginkgolide B:Aspirin=5:400), Composition 9 (Ginkgolide B:Aspirin=8:150), Composition 10 (Ginkgolide B:Aspirin=8:300), Composition 11 (Ginkgolide B:Aspirin=12:150), Composition 12 (Ginkgolide B:Aspirin=12:300). The preparation of composition 2-12 is:mixing Ginkgolide B and Aspirin.

1.3 Reagents and Instruments

Platelet activation factors (PAF) (cayman, lot number: 011219) was dissolved in the Tris-NaCl solution containing 0.25% of calf serum albumin at a pH of 7.6, to a final concentration of 3.6 nmoL/L; sodium citrate (Beijing Zhongshanjinqiao Biotechnology Company, lot number: 20130117) dissolved in the distilled water with 3.8% concentration; rabbit β-thromboglobulin (β-TG) ELISA kit (FOCUS, lot number: 20130224), rabbit platelet factor 4 (PF-4) (lot number: ELISA kit (FOCUS, lot number: 20130301). TYXN-96 multifunctional intelligent aggregometer (Shanghai General Technique Research Institute); Scanning electron microscope S-3000 N (Hitachi Limited); ELX-800 Absorbance Reader (BioTek Instruments, Inc.).

1.4 Groups and Administration Method

128 Japanese large-ear white rabbits were randomly assigned to 16 groups, with 8 rabbits in each group: (1) Saline group, (2) Ginkgolide B group, (3) Aspirin group, (4) Jinnaduo group, (5) Composition 1 group, (6) Composition 2 group, (7) Composition 3 group, (8) Composition 4 group, (9) Composition 5 group, (10) Composition 6 group, (11) Composition 7 group, (12) Composition 8 group, (13) Composition 9 group, (14) Composition 10 group, (15) Composition 11 group, (16) Composition 12 group. All groups were administered with a clinically used route and dosage for 7 days continuously. The dosage is showed in the following Table:

| Group | Dosage | Daily dosing frequency |
| --- | --- | --- |
| Saline | 2 ml | 1 |
| Ginkgolide B | 5.0 mg/kg | 1 |
| Aspirin | 5.0 mg/kg | 1 |
| Jinnaduo | 5.0 mg/kg | 1 |
| Composition 1 | 5.0 mg/kg | 1 |
| Composition 2 | 5.0 mg/kg | 1 |
| Composition 3 | 5.0 mg/kg | 1 |
| Composition 4 | 5.0 mg/kg | 1 |
| Composition 5 | 5.0 mg/kg | 1 |
| Composition 6 | 5.0 mg/kg | 1 |
| Composition 7 | 5.0 mg/kg | 1 |
| Composition 8 | 5.0 mg/kg | 1 |
| Composition 9 | 5.0 mg/kg | 1 |
| Composition 10 | 5.0 mg/kg | 1 |
| Composition 11 | 5.0 mg/kg | 1 |
| Composition 12 | 5.0 mg/kg | 1 |

1.5. Study of Platelet Aggregation Rate

After 7 days of administration, 10.5 ml of blood was taken from the heart of each animal, wherein 1.5 ml of plasma was used for taking serum and the rest 9 ml of plasma was subjected to 3.8% sodium citrate at 1:9 for anticoagulation, centrifuging for 10 minutes at 800 r/min, and taking the supernatant to obtain platelet-rich plasma (PRP).), wherein 100 µl of the PRP was taken for electron microscope examination, and the rest of the PRP was used for detecting of the platelet aggregation rate; the remaining portion was centrifuged for 15 min at a speed of 3000 r/min, and platelet-depleted plasma (PPP) was obtained. PPP was used to adjust the number of platelet in PRP, to be at $360\times10^9$/L. The platelet aggregation rate and maximum platelet aggregation rate was studied and recorded after 1 min, 5 min of addition of 10 µL of PAF.

1.6. Scanning Electron Microscopy Study of Platelet

The 100 µL of PRP was placed in a silicification EP tube, and 1 µL of PAF was added to induce aggregation of platelets for 15 minutes, the PRP was then placed on a copper mesh sample support laid with a Formar membrane, incubating at 37° C. for 10 min, washing with ultrapure water, fixing with 3% glutaraldehyde for 5 minutes, washing with ultrapure water. After the sample on the copper mesh was naturally dried, a layer of 20 nm gold film was plated on the surface of the sample, and the cell morphology was studied with an electron microscope S-3000N. 100 of platelets were observed, and calculated the ratio of each type of platelet. The types of platelet under the electron microscope includes: (1) Circle type appears circular or oval, with small size, compact center, large core and low and narrow transparent periphery zone. (2) Tree like type has a single or a plurality of elongated or sheet-shaped sometimes branched foot protrudes from the dense center. (3) Flat type has a dense core in the center and a wide transparent peripheral zone which has a smooth periphery or small bulges. (4) Aggregated-type is usually composed of several to dozens of platelets, with different sizes of the aggregates, wherein the platelets are mutually connected, some of the platelets are integrally fused into a whole, and the foot processes of the peripheral part are prominent.

1.7 Determination of PF-4 and β-TG Levels in Serum

1 µL of PAF was added to 1.5 mL of plasma for induction of release of PF-4 and β-TG. The plasma was rested at 4° C. for 4 hours, and 200 µL of serum was taken for detection. The specific operation is carried out according to the kit specification, and the result was read by the Absorbance Reader.

1.8 Statistical Analysis

The experimental results were showed in the form of mean value±standard deviation ($\bar{x}\pm s$). The statistical analysis is carried out using SPSS 18.0 software, and the platelet aggregation rates, the percentage of types of platelet morphology and the concentration of PF-4 and β-TG were analyzed using two-sample t-test. P-values<0.05 were considered statistically significant.

2. Results 2.1 Result of Platelet Aggregation Rate

There was a significant difference in the maximum platelet aggregation rate of the Ginkgolide B group, the Aspirin group, the Jinnaduo group and the Jinnaduo+Aspirin group and the Ginkgolide B+Aspirin group comparing with the saline group, under the induction of PAF ($p<0.01$, $p<<0.05$). The aggregation inhibition rate of each group is remarkably improved; the aggregation inhibition rate of the Ginkgolide B+Aspirin group is higher than the rate of Aspirin group, indicating the Ginkgolide B and Aspirin work synergistically; The mean aggregation inhibition rate of the Ginkgolide B+Aspirin groups is also higher than that of Composition 1 group (Jinnaduo+Aspirin), indicating the synergistic effect of Ginkgolide B and Aspirin is better than that of Jinnaduo and Aspirin.

TABLE 1

The aggregation effect of platelet inducing by PAF ($\bar{x} \pm s$, n = 8)

| Group | Dosage | 1 min | 5 min | MAX | Platelet aggregation inhibition rate (%) |
|---|---|---|---|---|---|
| Saline | 2 ml | 36.85 ± 6.14 | 68.32 ± 9.17 | 70.22 ± 11.40 | 0.00 |
| Ginkgolide B | 5.0 mg/kg | 21.36 ± 4.15** | 33.54 ± 5.48** | 38.86 ± 4.74** | 44.66 |
| Aspirin | 5.0 mg/kg | 25.28 ± 5.06* | 36.89 ± 5.53** | 48.08 ± 5.87** | 31.53 |
| Jinnaduo | 5.0 mg/kg | 30.51 ± 5.30* | 48.48 ± 8.79** | 51.60 ± 8.44** | 26.52 |
| Composition 1 | 5.0 mg/kg | 26.32 ± 4.07* | 38.90 ± 5.26** | 47.86 ± 4.53** | 31.84 |
| Composition 2 | 5.0 mg/kg | 24.34 ± 6.59** | 32.65 ± 7.26** | 33.70 ± 7.62** | 52.01 |
| Composition 3 | 5.0 mg/kg | 28.60 ± 6.08* | 48.46 ± 9.55** | 47.37 ± 9.58** | 32.54 |
| Composition 4 | 5.0 mg/kg | 25.43 ± 5.87* | 37.39 ± 8.08** | 46.84 ± 8.92** | 33.29 |
| Composition 5 | 5.0 mg/kg | 26.27 ± 6.08* | 37.73 ± 8.46** | 41.96 ± 9.50** | 40.24 |
| Composition 6 | 5.0 mg/kg | 20.37 ± 5.89** | 31.67 ± 8.48** | 35.43 ± 7.49** | 49.54 |
| Composition 7 | 5.0 mg/kg | 25.09 ± 5.26* | 34.95 ± 7.63** | 40.71 ± 7.25** | 42.03 |
| Composition 8 | 5.0 mg/kg | 22.16 ± 5.42** | 34.01 ± 7.50** | 42.69 ± 7.26** | 39.21 |
| Composition 9 | 5.0 mg/kg | 22.65 ± 5.48** | 26.84 ± 5.37** | 37.28 ± 5.66** | 46.91 |
| Composition 10 | 5.0 mg/kg | 25.58 ± 7.00* | 42.66 ± 5.59** | 47.02 ± 6.37** | 33.04 |
| Composition 11 | 5.0 mg/kg | 40.40 ± 7.39 | 41.52 ± 7.32** | 40.29 ± 7.58* | 42.62 |
| Composition 12 | 5.0 mg/kg | 24.42 ± 5.04** | 30.84 ± 7.22** | 39.49 ± 7.38** | 43.76 |

Comparing with Saline group, **p < 0.01, *p < 0.05

2.2. Result of Electron Microscope Study of Platelets

Four types of platelet morphology were observed under 2000-fold scanning electron microscope: Circle type, Tree like type, Flat type and Aggregated type. Under induction of PAF, the platelets were in a similar size and had a smooth surface in the Ginkgolide B group, the Jinnaduo group, the Jinnaduo+Aspirin group and the Ginkgolide B+Aspirin group, and the Aggregated type platelets were rarely seen. The platelets in the saline group were strongly activated, with enhanced adhesion, and red blood cells can be seen to adhere to the platelets; the platelets were irregular in shape with enlarged size, and the formation of spore-like pseudopodium and increased number of Aggregated type of platelets were observed. The platelets in the Aspirin group are various in size with pseudopodium on the surface and increased number of Aggregated type platelets. In the view of the above result, the Ginkgolide B and Aspirin have a synergistic effect. The Aggregated type platelets are less in the Ginkgolide B+Aspirin group than in the Jinnaduo+Aspirin group, indicating the synergistic effect of Ginkgolide B and Aspirin is greater than the synergistic effect of Jinnaduo and Aspirin.

2.3 Result of the Level of PF-4 and β-TG

Compared with the saline group, the levels of PF-4 of the Ginkgolide B group, the Jinnaduo+Aspirin group and the Ginkgolide B+Aspirin group decreased significantly (p<0.01, p<0.05); the levels of β-TG of the Ginkgolide B group, the Jinnaduo group, the Jinnaduo+Aspirin group and the Ginkgolide B+Aspirin group decreased significantly (p<0.01, p<0.05), while the level of the Aspirin group didn't decrease significantly. In view of the above result, both Ginkgolide B and Jinnaduo work with Aspirin synergistically; Since the level of PF-4 and β-TG is lower in the Ginkgolide B+Aspirin group than in the Jinnaduo+Aspirin group, indicating the synergistic effect of Ginkgolide B and Aspirin is greater than the synergistic effect of Jinnaduo and Aspirin, and the platelet release function is inhibited.

TABLE 3

The level of PF-4 and β-TG ($\bar{x} \pm s$, n = 8)

| Group | PF-4 (μg/ml) | β-TG (μg/ml) |
|---|---|---|
| Saline | 1.733 ± 0.294 | 1.740 ± 0.215 |
| Ginkgolide B | 1.264 ± 0.215** | 1.247 ± 0.184** |

TABLE 2

Morphology of platelets of each group after the addition of PAF ($\bar{x} \pm s$, n = 8)

| Group | Types of morphology (%) | | | |
|---|---|---|---|---|
| | Circle | Tree like | Flat | Aggregated |
| Saline | 3.2 ± 0.8 | 7.5 ± 2.4 | 11.8 ± 3.2 | 77.5 ± 18.5 |
| Ginkgolide B | 31.6 ± 6.4** | 15.8 ± 6.8* | 46.1 ± 8.3** | 22.3 ± 9.6** |
| Aspirin | 5.8 ± 2.6 | 14.7 ± 7.0* | 25.5 ± 8.4** | 54.0 ± 14.3* |
| Jinnaduo | 11.2 ± 9.6** | 23.4 ± 9.0** | 35.8 ± 11.0** | 29.6 ± 10.4** |
| Composition 1 | 34.0 ± 11.5** | 14.7 ± 9.2* | 23.6 ± 8.2** | 27.7 ± 12.5** |
| Composition 2 | 28.0 ± 8.3** | 12.6 ± 6.8* | 50.3 ± 7.0** | 9.1 ± 15.2** |
| Composition 3 | 24.2 ± 7.5** | 21.4 ± 9.4** | 33.6 ± 10.7** | 20.8 ± 11.1** |
| Composition 4 | 18.8 ± 1.0** | 22.3 ± 4.7** | 37.6 ± 6.5** | 21.3 ± 16.0** |
| Composition 5 | 19.7 ± 7.8 | 24.6 ± 8.8** | 30.7 ± 13.6** | 25.0 ± 14.9** |
| Composition 6 | 33.5 ± 12.6** | 18.8 ± 8.3** | 36.2 ± 14.4** | 11.5 ± 3.3** |
| Composition 7 | 29.8 ± 12.1** | 29.2 ± 8.0** | 28.9 ± 11.5** | 12.10 ± 4.6** |
| Composition 8 | 40.7 ± 15.3** | 15.5 ± 6.0 | 18.7 ± 7.8 | 25.1 ± 10.0** |
| Composition 9 | 40.3 ± 10.2** | 20.6 ± 9.6* | 22.4 ± 9.0* | 16.7 ± 8.8** |
| Composition 10 | 30.8 ± 10.1** | 19.5 ± 6.9** | 25.3 ± 10.2** | 24.4 ± 3.5** |
| Composition 11 | 27.9 ± 11.7** | 20.4 ± 9.5** | 32.3 ± 8.6** | 19.4 ± 10.7** |
| Composition 12 | 30.7 ± 12.1** | 20.4 ± 8.0** | 27.8 ± 11.5** | 21.1 ± 4.6** |

Comparing with Saline group, **p < 0.01, *p < 0.05

TABLE 3-continued

The level of PF-4 and β-TG ($\bar{x} \pm s$, n = 8)

| Group | PF-4 (μg/ml) | β-TG (μg/ml) |
|---|---|---|
| Aspirin | 1.489 ± 0.228 | 1.504 ± 0.244 |
| Jinnaduo | 1.525 ± 0.170 | 1.472 ± 0.153* |
| Composition 1 | 1.301 ± 0.203* | 1.465 ± 0.268* |
| Composition 2 | 1.177 ± 0.144** | 1.129 ± 0.158** |
| Composition 3 | 1.251 ± 0.245* | 1.402 ± 0.243* |
| Composition 4 | 1.214 ± 0.225** | 1.346 ± 0.214* |
| Composition 5 | 1.276 ± 0.216* | 1.388 ± 0.209 |
| Composition 6 | 1.170 ± 0.186** | 1.394 ± 0.176** |
| Composition 7 | 1.274 ± 0.139* | 1.236 ± 0.170** |
| Composition 8 | 1.289 ± 0.215* | 1.396 ± 0.231* |
| Composition 9 | 1.245 ± 0.175** | 1.216 ± 0.134** |
| Composition 10 | 1.268 ± 0.151* | 1.342 ± 0.150* |
| Composition 11 | 1.216 ± 0.117* | 1.204 ± 0.165** |
| Composition 12 | 1.203 ± 0.162** | 1.203 ± 0.162** |

Comparing with Saline group, **p < 0.01, *p < 0.05

The results show that combination use of Ginkgolide B and Aspirin can effectively reduce the platelet aggregation rate, decrease the number of Aggregated type platelets, down-regulate the level of PF-4 and β-TG, indicating the aggregation of platelets is inhibited, and an anti-platelet aggregation medicine with good effect can be prepared using the Ginkgolide B and Aspirin. The combination use of Ginkgolide B and Aspirin is obviously superior to using Ginkgolide B or Aspirin alone, indicating these two work synergistically.

In conclusion, the combination use of Ginkgolide B and Aspirin results in synergistic effect, and good anti-platelet aggregation effect. The pharmaceutical composition comprising Ginkgolide B and Aspirin effectively inhibit the aggregation of platelets, with promising clinical application.

The invention claimed is:

1. A pharmaceutical composition comprising:
   Ginkgolide B in an amount of 10 parts by weight, and
   Aspirin in an amount of 200 parts by weight.

2. A method for preparing the pharmaceutical composition of claim 1, comprising:
   weighing out 10 parts by weight of the Ginkgolide B and 200 parts by weight of the Aspirin;
   mixing the Ginkgolide B and the Aspirin, and
   adding a pharmaceutically acceptable auxiliary to prepare the pharmaceutical composition.

3. A method for inhibiting platelet aggregation, comprising:
   administering a pharmaceutical composition to a subject requiring platelet aggregation inhibition, the pharmaceutical composition comprising:
   Ginkgolide B in an amount of 10 parts by weight, and
   Aspirin in an amount of 200 parts by weight.

* * * * *